United States Patent [19]

Mullin, Jr. et al.

[11] Patent Number: 4,891,429
[45] Date of Patent: Jan. 2, 1990

[54] ANTIARRHYTHMIC AGENTS

[75] Inventors: John G. Mullin, Jr., Hawthorne, N.J.; Keiji Nakamura, Kamakura, Japan; Jefferson W. Tilley, North Caldwell, N.J.; Hiroshi Watanabe, Chigasaki, Japan

[73] Assignee: Hoffmann-La Roche Inc., Nutley, N.J.

[21] Appl. No.: 62,028

[22] Filed: Jun. 15, 1987

Related U.S. Application Data

[62] Division of Ser. No. 722,650, Apr. 12, 1985, Pat. No. 4,696,930.

[51] Int. Cl.$^4$ .............................................. C07D 213/38
[52] U.S. Cl. ...................................... 546/329; 544/242; 548/341; 548/342
[58] Field of Search ................ 546/329; 548/341, 342; 544/242

[56] References Cited

U.S. PATENT DOCUMENTS

| | | | |
|---|---|---|---|
| 3,646,045 | 2/1972 | Berger et al. | 546/329 |
| 4,328,029 | 5/1982 | Thomas et al. | 71/92 |
| 4,336,059 | 6/1982 | Ziman | 71/90 |
| 4,338,119 | 7/1982 | Stetter et al. | 71/92 |
| 4,415,587 | 11/1983 | Diamond et al. | 514/625 |

Primary Examiner—Mary C. Lee
Assistant Examiner—Z. Northington-Davis
Attorney, Agent, or Firm—George M. Gould; Bernard S. Leon; Matthew Boxer

[57] ABSTRACT

Compounds of the formula

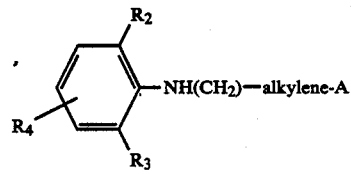

wherein $R_2$, $R_3$ and $R_4$ are independently, hydrogen or methyl; A is 3-pyridinyl which is unsubstituted, or substituted by lower alkyl, phenyl, or naphthyl, are described.

The compounds of the invention are intermediates in the preparation of antiarrhythmic agents.

2 Claims, No Drawings

ANTIARRHYTHMIC AGENTS

This is a division, of application Ser. No. 722,650, filed Apr. 12, 1985, now U.S. Pat. No. 4,696,930.

BRIEF SUMMARY OF THE INVENTION

The invention relates to a compound of the formula

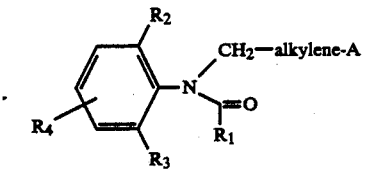

wherein $R_1$ is -alkylene'-$NH_2$ or -alkylene'-A'; $R_2$, $R_3$ and $R_4$ are, independently, hydrogen or methyl; A and A' are, independently, unsubstituted or lower alkyl or aryl substituted pyridinyl, imidazolyl, or pyrimidinyl; and, when an asymmetric carbon is present, an enantiomer thereof, or a racemic mixture thereof; or a pharmaceutically acceptable salt thereof.

The compounds of formula I are useful as antiarrhythmic agents.

DETAILED DESCRIPTION OF THE INVENTION

As used herein, the term "lower alkyl" denotes an alkyl of 1-5 carbon atoms which may be straight or branch chained, for example, methyl, ethyl, propyl, butyl, methylethyl, and the like. The terms "alkylene" and "alkylene'" denote a straight chain alkylene of 1-5 carbon atoms optionally substituted with one or more lower alkyl substituents, for example, methylene, ethylene, propylene, isobutylene, methylethylene, butylpropylene and the like. Alkylene and alkylene' may be the same or different. The term "aryl" denotes a hydrocarbon ring system, such as, phenyl or naphthyl with phenyl being preferred. The term "halo" or "halide" denotes a halogen such as iodine, chlorine, bromine or fluorine. The term "rac." denotes a racemic mixture.

The invention relates to a compound of the formula

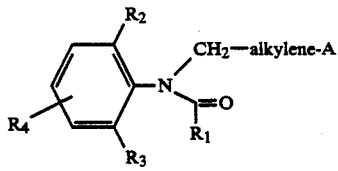

wherein $R_1$ is -alkylene'-$NH_2$ or -alkylene'-A'; $R_2$, $R_3$ and $R_4$ are, independently, hydrogen or methyl; A and A' are, independently, unsubstituted or lower alkyl or aryl substituted pyridinyl, imidazolyl, or pyrimidinyl; and, when an asymmetric carbon is present, an enantiomer thereof, or a racemic mixture thereof; or a pharmaceutically acceptable salt thereof.

The compounds of formula I are useful as antiarrhythmic agents.

A preferred compound of the invention is a compound of the formula I wherein $R_1$ is -alkylene'-$NH_2$,

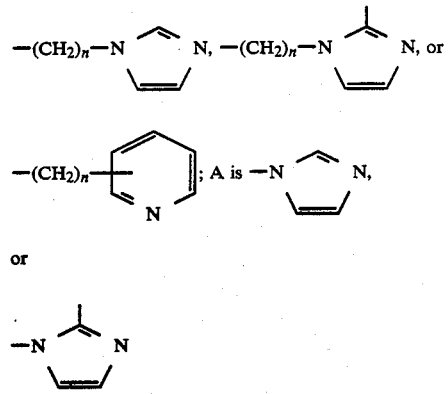

2-, 3- or 4-pyridinyl; wherein the alkylene attached to A is straight chain alkylene of 1 to 5 carbon atoms; n is an integer from 1 to 5; and when an asymmetric carbon is present, an enantiomer thereof, or a racemic mixture thereof; or a pharmaceutically acceptable salt thereof.

A more preferred compound of the invention is a compound of formula I, as described just above, wherein $R_1$ is

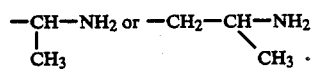

and A is 3-pyridinyl.

A still more preferred compound of the invention is a compound of formula I, as described just above, wherein $R_1$ is

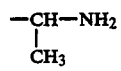

and the alkylene attached to A is of 2 or 5 carbon atoms.

Examplary of compounds of formula I are:
rac.-2-amino-N-(2,6-dimethylphenyl)-N-[2-(1H-imidazol-1-yl) ethyl]propanamide;
rac.-2-amino-N-(2,6-dimethylphenyl)-N-[3-(1H-imidazol-1-yl) propyl]propanamide;
rac.-2-amino-N-(2,6-dimethylphenyl)-N-[4-(1H-imidazol-1-yl) butyl]propanamide;
rac.-2-amino-N-(2,6-dimethylphenyl)-N-[5-(1H-imidazol-1-yl) pentyl]propanamide;
rac.-2-amino-N-(2,6-dimethylphenyl)-N-[6-(1H-imidazol-1-yl) hexyl]propanamide;
rac.-3-amino-N-(2,6-dimethylphenyl)-N-[2-(3-pyridinyl)-ethyl]butanamide;
rac.-3-amino-N-(2,6-dimethylphenyl)-N-[2-(4-pyridinyl)-ethyl]butanamide;
rac.-3-amino-N-(2,6-dimethylphenyl)-N-[3-(3-pyridinyl)-propyl]butanamide;
rac.-3-amino-N-(2,6-dimethylphenyl)-N-[3-(4-pyridinyl)-propyl]butanamide;
rac.-3-amino-N-(2,6-dimethylphenyl)-N-[4-(3-pyridinyl)-butyl]butanamide;
rac.-3-amino-N-(2,6-dimethylphenyl)-N-[4-(4-pyridinyl)-butyl]butanamide;
rac.-3-amino-N-(2,6-dimethylphenyl)-N-[5-(3-pyridinyl)-pentyl]butanamide;
rac.-3-amino-N-(2,6-dimethylphenyl)-N-[5-(4-pyridinyl)-pentyl]butanamide;

rac.-3-amino-N-(2,6-dimethylphenyl)-N-[6-(3-pyridinyl)-hexyl]butanamide;
rac.-3-amino-N-(2,6-dimethylphenyl)-N-[6-(4-pyridinyl)-hexyl]butanamide;
N-(2,6-dimethylphenyl)-N-[2-(3-pyridinyl)ethyl]-1H-imidazole -1-acetamide;
N-(2,6-dimethylphenyl)-N-[2-(4-pyridinyl)ethyl]-1H-imidazole -1-acetamide;
N-(2,6-dimethylphenyl)-N-[3-(3-pyridinyl)propyl]1H-imidazole -1-acetamide;
N-(2,6-dimethylphenyl)-N-[3-(4-pyridinyl)propyl]-1H-imidazole-1-acetamide;
N-(2,6-dimethylphenyl)-N-[4-(3-pyridinyl)butyl]-1H-imidazole-1-acetamide;
N-(2,6-dimethylphenyl)-N-[4-(4-pyridinyl)butyl]-1H-imidazole-1-acetamide;
N-(2,6-dimethylphenyl)-N-[5-(3-pyridinyl)pentyl]-1H-imidazole -1-acetamide;
N-(2,6-dimethylphenyl)-N-[5-(4-pyridinyl)pentyl]-1H-imidazole -1-acetamide;
N-(2,6-dimethylphenyl)-N-[6-(3-pyridinyl)hexyl]-1H-imidazole -1-acetamide;
N-(2,6-dimethylphenyl)-N-[6-(4-pyridinyl)hexyl]-1H-imidazole -1-acetamide;
N-(2,6-dimethylphenyl)-2-methyl-N-[2-(3-pyridinyl)ethyl]-1H -imidazole-1-acetamide;
N-(2,6-dimethylphenyl)-2-methyl-N-[2-(4-pyridinyl)ethyl]-1H -imidazole-1-acetamide;
N-(2,6-dimethylphenyl)-2-methyl-N-[3-(3-pyridinyl)propyl]-1H-imidazole-1-acetamide;
N-(2,6-dimethylphenyl)-2-methyl-N-[3-(4-pyridinyl)propyl]-1H-imidazole-1-acetamide;
N-(2,6-dimethylphenyl)-2-methyl-N-[4-(3-pyridinyl)butyl]-1H -imidazole-1-acetamide;
N-(2,6-dimethylphenyl)-2-methyl-N-[4-(4-pyridinyl)butyl]-1H -imidazole-1-acetamide;
N-(2,6-dimethylphenyl)-2-methyl-N-[5-(3-pyridinyl)pentyl]-1H-imidazole-1-acetamide;
N-(2,6-dimethylphenyl)-2-methyl-N-[5-(4-pyridinyl)pentyl]-1H-imidazole-1-acetamide;
N-(2,6-dimethylphenyl)-2-methyl-N-[6-(3-pyridinyl)hexyl]-1H -imidazole-1-acetamide;
N-(2,6-dimethylphenyl)-2-methyl-N-[6-(4-pyridinyl)hexyl]-1H -imidazole-1-acetamide;
N-(2,6-dimethylphenyl)-N-[2-(1H-imidazol-1yl)ethyl]-3-pyridinebutanamide;
N-(2,6-dimethylphenyl)-N-[3-(1H-imidazol-1-yl)propyl]-3-pyridinebutanamide;
N-(2,6-dimethylphenyl)-N-[4-(1H-imidazol-1-yl)butyl]-3-pyridinebutanamide;
N-(2,6-dimethylphenyl)-N-[5-(1H-imidazol-1-yl)pentyl]-3-pyridinebutanamide;
N-(2,6-dimethylphenyl)-N-[6-(1H-imidazol-1-yl)hexyl]-3-pyridinebutanamide;
rac.-2-amino-N-(2,6-dimethylphenyl)-N-[2-(3-pyridinyl)-ethyl]propanamide;
rac.-2-amino-N-(2,6-dimethylphenyl)-N-[2-(4-pyridinyl)-ethyl]propanamide;
rac.-2-amino-N-(2,6-dimethylphenyl)-N-[3-(4-pyridinyl)-propyl]propanamide;
rac.-2-amino-N-(2,6-dimethylphenyl)-N-[4-(4-pyridinyl)-butyl]propanamide;
rac.-2-amino-N-(2,6-dimethylphenyl)-N-[5-(3-pyridinyl)-pentyl]propanamide;
rac.-2-amino-N-(2,6-dimethylphenyl)-N-[5-(4-pyridinyl)-pentyl]propanamide;
rac.-2-amino-N-(2,6-dimethylphenyl)-N-[6-(4-pyridinyl)-hexyl]propanamide;

N-(2,6-dimethylphenyl)-N-[5-(3-pyridinyl)pentyl]-3-pyridine -butanamide;
N-(2,6-dimethylphenyl)-N-[5-(4-pyridinyl)pentyl]-3-pyridine -butanamide;
N-(2,6-dimethylphenyl)-N-[6-(3-pyridinyl)hexyl]-3-pyridine -butanamide;
N-(2,6-dimethylphenyl)-N-[6-(4-pyridinyl)hexyl]-3-pyridine -butanamide;
rac.-3-amino-N-(2,6-dimethylphenyl)-N-[2-(1H-imidazol-1-yl) ethyl]butanamide;
rac.-3-amino-N-(2,6-dimethylphenyl)-N-[3-(1H-imidazol-1-yl) propyl]butanamide;
rac.-3-amino-N-(2,6-dimethylphenyl)-N-[4-(1H-imidazol-1-yl) butyl]butanamide;
rac.-3-amino-N-(2,6-dimethylphenyl)-N-[5-(1H-imidazol-1-yl) pentyl]butanamide;
rac.-3-amino-N-(2,6-dimethylphenyl)-N-[6-(1H-imidazol-1-yl) hexyl]butanamide;
rac.-2-amino-N-(2,6-dimethylphenyl)-N-[3-(3-pyridinyl)-propyl]butanamide;
N-(2,4,6-trimethylphenyl)-N-[5-(3-pyridinyl)pentyl]-3-pyridinebutanamide;
N-(4-methylphenyl)-N-[5-(3-pyridinyl)pentyl]-3-pyridine-butanamide;
N-(2,6-dimethylphenyl)-N-[5-(5-pyrimidinyl)pentyl]-3-pyridinebutanamide;
N-(2,6-dimethylphenyl)-N-[2-(1H-imidazol-1yl)ethyl]-1H-imidazole -1-acetamide;
N-(2,6-dimethylphenyl)-N-[3-(1H-imidazol-1-yl)propyl]-1H-imidazole -1-acetamide;
N-(2,6-dimethylphenyl)-N-[4-(1H-imidazol-1-yl)butyl]-1H-imidazole -1-acetamide;
N-(2,6-dimethylphenyl)-N-[5-(1H-imidazol-1yl)pentyl]-1H-imidazole -1-acetamide;
N-(2,6-dimethylphenyl)-N-[6-(1H-imidazol-1-yl)hexyl]-1H-imidazole -1-acetamide;
N-(2,6-dimethylphenyl)-α-methyl-N-[2-(1H-imidazol-1-yl) -ethyl]-1H-imidazole-1-acetamide;
N-(2,6-dimethylphenyl)-α-methyl-N-[3(1H-imidazol-1-yl) propyl]-1H-imidazole-1-acetamide;
N-(2,6-dimethylphenyl)-α-methyl-N-[4-(1H-imidazol-1-yl) -butyl]-1H-imidazole-1-acetamide;
N-(2,6-dimethylphenyl)-α-methyl-N-[5-(1H-imidazol-1-yl) -pentyl]-1H-imidazole-1-acetamide;
N-(2,6-dimethylphenyl)-α-methyl-N-[6-(1H-imidazol-1-yl) -hexyl]-1H-imidazole-1-acetamide;
N-(2,6-dimethylphenyl)-N-[2-(3-pyridinyl)ethyl]-3-pyridine -butanamide;
N-(2,6-dimethylphenyl)-α-methyl-N-[5-(1H-imidazol-1-yl) -3,3-dimethylpentyl]-1H-imidazole-1-acetamide;
N-[2-(1H-imidazol-1-yl)ethyl]-N-(2,6-dimethylphenyl)-β-methyl -3-pyridinebutanamide;
N-(2,6-dimethylphenyl)-N-[2-(4-pyridinyl)ethyl]-3-pyridinebutamide;
N-(2,6-dimethylphenyl)-N-[3-(3-pyridinyl)propyl]-3-pyridinebutanamide;
N-(2,6-dimethylphenyl)-N-[3-(4-pyridinyl)propyl]-3-pyridinebutanamide;
N-(2,6-dimethylphenyl)-N-[4-(3-pyridinyl)butyl]-3-pyridinebutanamide;
N-(2,6-dimethylphenyl)-N-[4-(4-pyridinyl)butyl]-3-pyridinebutanamide;
rac.-2-amino-N-phenyl-N-[3-(3-pyridinyl)propyl]-propanamide;
rac.-2-amino-N-(4-methylphenyl)-N-[3-(3-pyridinyl)propyl]propanamide;
rac.-2-amino-N-(2,6-dimethylphenyl)-N-[6-(5-pyrimidinyl) hexyl]propanamide; and rac.-2-amino-N-(2,6-dimethylphenyl)-N-[3-methyl-6-(3-pyridinyl) hexyl]propanamide.

Preferred compounds of formula I are:

rac.-2-amino-N-(2,6-dimethylphenyl)-N-[4-(3-pyridinyl)-butyl]propanamide; and rac.-2-amino-N-(2,6-dimethylphenyl)-N-[6-(3-pyridinyl)-hexyl]propanamide.

A most preferred compound of formula I is:

rac.-2-amino-N-(2,6-dimethylphenyl)-N-[3-(3-pyridinyl)-propyl]propanamide.

The compounds of formula I are useful as antiarrhythmic agents. Furthermore, the compounds of formula I are useful as antithrombotic agents. The compounds of formula I also inhibit thromboxane synthase and therefore are useful in the treatment of ischemic heart disease. Some of the compounds of formula I also have blood platelet antiaggregatory properties.

The invention also relates to a compound of the formula

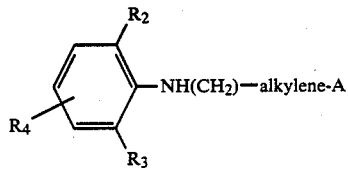

wherein $R_2$, $R_3$ and $R_4$ are, independently, hydrogen or methyl. A is unsubstituted or lower alkyl or aryl substituted pyridinyl, imidazolyl, or pyrimidinyl.

More preferred is a compound of formula VI, as described just above, wherein A is unsubstituted or lower alkyl or aryl substituted 3-pyridinyl.

Exemplary of a compound of formula VI is N-(2,6-dimethylphenyl)-3-pyridinepropanamine.

In reaction scheme 1, there is diagrammed a process for preparing compounds of formula VI and VI' which are intermediates in preparing compounds of formula I of the invention.

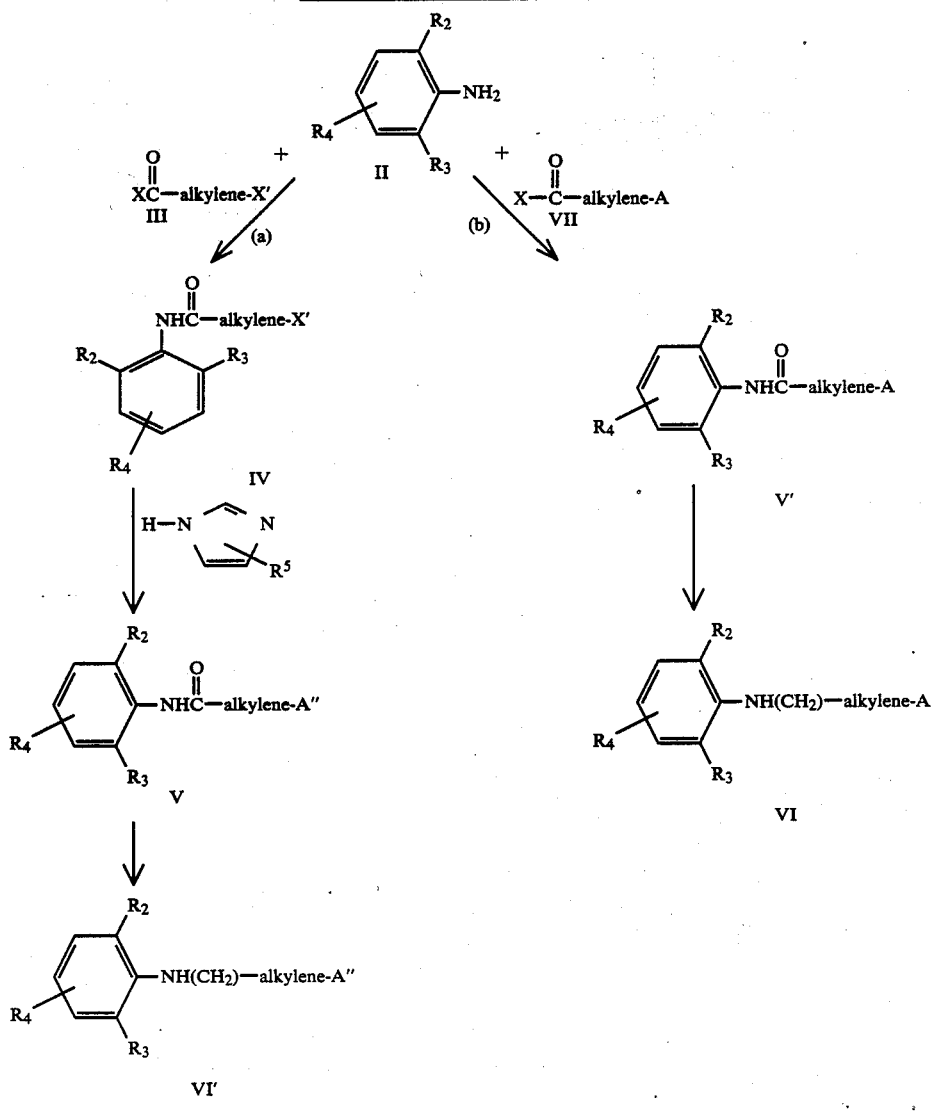

REACTION SCHEME 1 wherein $R_2$, $R_3$ and $R_4$ are independently hydrogen or methyl; $R_5$ is hydrogen, lower alkyl, or aryl; X and X' are independently halo; A" is unsubstituted or lower alkyl or aryl substituted imidazolyl; and A is unsubstituted or lower alkyl or aryl substituted imidazolyl, pyridinyl or pyrimidinyl.

Compounds of formula II are known compounds or can be prepared by known methods.

Exemplary of compounds of formula II are
aniline;
2-methylaniline;
2,6-dimethylaniline;
2,4,6-trimethylaniline;
4-methylaniline; and the like.

Compounds of formula III are known compounds or can be prepared by known methods.

A compound of formula II can be converted to a compound of formula IV by reaction with a compound of formula III per reaction path (a) of Reaction Scheme 1.

Thus, a compound of formula II, in an aprotic organic solvent, is added to a reaction vessel which already is charged with a reaction mixture containing a compound of formula III. The polar organic solvent which is employed can be selected from the group consisting of chloroform, methylene chloride, or most preferably, dimethylformamide. The resulting solution is stirred for about 10 to about 120 minutes.

The resulting compound of formula IV can be recovered by conventional means. For example, the organic solvent in the reaction mixture can be evaporated, and the residue can be partitioned between an organic solvent and an aqueous layer. The organic solvent used for partitioning can be selected from the group consisting of chloroform, ethyl acetate, or most preferably methylene chloride. The aqueous layer can be selected from saturated potassium bicarbonate, or more preferably saturated sodium bicarbonate. The organic layer can be dried over sodium sulfate, or more preferably potassium carbonate and evaporated to obtain the compound of formula IV.

Exemplary of compounds of formula IV which can be prepared by this method are:
2-chloro-N-(2,6-dimethylphenyl)acetamide;
3-bromo-N-(2,6-dimethylphenyl)propanamide;
5-chloro-N-(2,6-dimethylphenyl)pentanamide; and the like.

A compound of formula IV can be converted to a compound of formula V by reaction with a substituted or unsubstituted imidazole. For example, 2-chloro-N-(2,6-dimethylphenyl) acetamide, a compound of formula IV, can be converted to N-(2,6-dimethyl)-1H-imidazole-1-acetamide, a compound of formula V, by reaction with an alkali metal hydride and imidazole.

The reaction can be carried out, by adding 2-chloro-N-(2,6-dimethylphenyl) acetamide to a heated mixture of sodium hydride and imidazole in an aprotic organic solvent, preferably dimethylformamide. The temperature of the reaction which is not critical can be about 50°. The reaction is continued until the formation of N-(2,6-dimethylphenyl)-1H-imidazole-1-acetamide is complete.

Water is added to the reaction mixture, which is then evaporated to dryness. The residue is then dissolved in an acid, such as hydrochloric acid, washed with a solvent, such as ether, made basic, and extracted with a solvent such as dichloromethane.

N-(2,6-dimethylphenyl)-1H-imidazole-1-acetamide can be recovered by conventional means such as crystallization.

Exemplary of compounds of formula V are:
N-(2,6-dimethylphenyl)-1H-imidazole-1-butanamide;
N-(2,6-dimethylphenyl)-1H-imidazole-1-acetamide; and the like.

A compound of formula V can be converted to a compound of formula VI' by reaction with a reducing agent such as lithium aluminum hydride or more preferably borane in an aprotic solvent such as for example, tetrahydrofuran. The reaction is conducted to about the reflux temperature of the solvent employed. The reaction is conducted from about 1½ to about 24 hours. If borane is used as the reducing agent, decomposition of borane remaining after the reaction is accomplished by cooling the reaction mixture; adding a proton source such as ethanol, or more preferably methanol. This product can be isolated by making the reaction mixture strongly acidic, by adding for example hydrochloric acid, in order to decompose boron complexes; making the reaction mixture basic with, for example, an alkali metal hydroxide; and extracting with a suitable organic solvent such as methylene chloride.

The resulting compound of formula VI' can be recovered by conventional means, such as, for example, formation of the (E)-2-butenedioate salt.

Exemplary of the compounds of formula VI' prepared by this reaction are:
N-(2,6-dimethylphenyl)-1H-imidazole-1-butanamine;
N-(2,6-dimethylphenyl)-1H-imidazole-1-ethanamine;
and the like.

Alternately, a compound of formula VI can be prepared by carrying out reaction path (b) of Reaction Scheme 1.

Thus a compound of formula II is converted to a compound of formula V' by reaction with a compound of formula VII.

Compounds of formula VII are known or can be prepared by known methods, for example, the reaction of the corresponding acids, which are either known or can be prepared by known methods, with an acid halide forming reagent such as oxalyl chloride, or more preferably phosphorous trichloride, or thionyl halides such as, thionyl bromide, or more preferably thionyl chloride.

The carboxylic acid corresponding to the pyrimidine-, imidazole- or pyridinealkanoylhalide to be formed and the reagent for generating the acid halide can be stirred together until acid halide formation is complete. The temperature at which said reaction is conducted is not critical. The residual reagent can be removed by evaporation and dissolution of the residue in a non-polar, aromatic organic solvent such as toluene and reevaporating the resulting mixture. In one embodiment of the above reaction, 3-pyridinehexanoyl chloride is generated by the reaction of thionyl chloride and 3-pyridine hexanoic acid.

Exemplary of the compounds of formula VII which are thus generated are:
3-pyridinehexanoyl chloride;
3-pyridinebutanoyl chloride;
4-pyridinebutanoyl chloride;
4-pyridinepropanoyl chloride
1H-imidazole-1-hexanoyl chloride;
1H-imidazole-1-propanoyl chloride;
1H-imidazole-1-ethanoyl chloride; and the like.

A compound of formula II is converted to a compound of formula V' by reaction with a compound of formula VII. Thus a mixture of a compound of formula II in a polar organic solvent is added to a reaction vessel containing a freshly prepared acid halide of formula VII. The polar organic solvent which is employed can be selected from the group consisting of chloroform, methylene chloride, or most preferably, dimethylformamide. The resulting solution is stirred for about 10 to about 20 minutes.

The resulting compound of formula V' can be recovered by conventional means. For example, the organic solvent in the reaction mixture can be evaporated, and the residue can be partitioned between an organic solvent and an aqueous layer. The organic solvent used for partitioning can be selected from the group consisting of chloroform, ethyl acetate, or most preferably methylene chloride. The aqueous layer can be selected from saturated potassium bicarbonate, or more preferably saturated sodium bicarbonate. The organic layer can be dried over sodium sulfate, or more preferably potassium carbonate and evaporated to a compound of formula V'.

Exemplary of compounds of formula V' formed by the just above described reaction are:

N-phenyl-5-pyrimidinepropanamide;
N-phenyl-3-pyridinepropanamide;
N-(2,6-dimethylphenyl)-1H-imidazole-1-butanamide;
N-(4-methylphenyl)-3-pyridinepropanamide;
N-(2,6-dimethylphenyl)-3-pyridinepropanamide;
N-(2,6-dimethylphenyl)-3-pyridinebutanamide; and the like.

Conversion of a compound of formula V' to a compound of formula VI can be performed in an analogous manner to the conversion of a compound of formula V to a compound of formula VI' described above.

Exemplary of compounds of formula VI formed through reaction path (b) are:

N-(2,6-dimethylphenyl)-1H-imidazole-1-ethanamine;
N-phenyl-5-pyrimidinebutanamine;
N-phenyl-3-pyridinebutanamine;
N-(4-methylphenyl-3-pyridinebutanamine;
N-(2,6-dimethylphenyl)-3-pyridinebutanamine,
N-(2,6-dimethylphenyl)-3-pyridinebutanamine; and the like.

In reaction scheme 2 there is diagrammed a process for preparing compounds of formula VI" which are intermediates in preparing compounds of formula I of the invention.

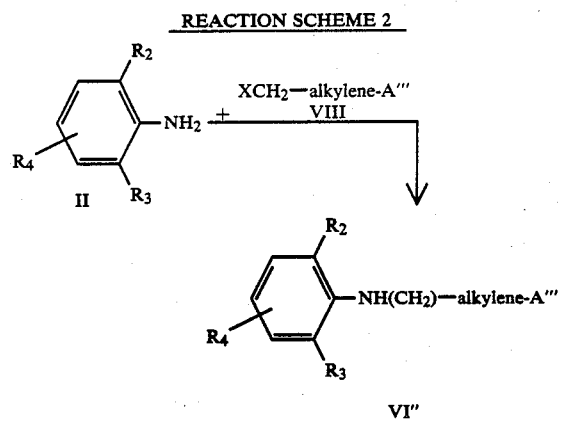

REACTION SCHEME 2 wherein $R_2$, $R_3$, $R_4$ and X are as described above; and A''' is unsubstituted or lower alkyl or aryl substituted pyridinyl or pyrimidinyl.

Exemplary, of compounds of formula VIII are 3-pyridinepropyl bromide; 2-pyrimidinehexyl chloride; and the like.

Compounds of formula VIII are known or can be prepared by known methods. Acid addition salts of these compounds may be used in the reaction. A preferred compound of formula VIII is 3-pyridinepropyl bromide hydrobromide.

In the reaction, an excess of a compound of formula II can be reacted with a compound of formula VIII at a temperature in the range of from about 130° to about 170°. The reaction is run from about one and a half to about three and a half hours.

Separation of the compound of formula VI" can be achieved by conventional techniques. For example, the excess of the compound of formula II can be removed from the reaction mixture by distillation. The residue is dissolved in a non-polar aromatic solvent and base. The non-polar, aromatic solvent can be selected from the group consisting of benzene, toluene, xylene, ethylbenzene and isobutylbenzene. A preferred non-polar, aromatic solvent is toluene. The base can be aqueous alkali metal hydroxide or aqueous alkali metal carbonate, such as sodium carbonate. The aqueous layer is extracted with a non-polar, aromatic solvent such as toluene and the combined organic layers are washed with an aqueous base such as potassium carbonate, or more preferably sodium hydroxide, and then washed with a saturated salt solution such as aqueous sodium chloride, and dried over sodium sulfate, or more preferably potassium carbonate. Evaporation of the organic solvent and purification, if necessary, by crystallization or chromatography yields the compound of formula VI".

The compounds of formulas VI' and VI" are subgeneric to the compounds of formula VI. Accordingly, reaction schemes 3 and 4 which follow, and which begin with a compound of formula VI, necessarily encompass compounds of formulas VI' and VI".

A compound of formula VI can be converted into a compound of formula Ia or Ib as shown schematically in Reaction Scheme 3 below.

REACTION SCHEME 3

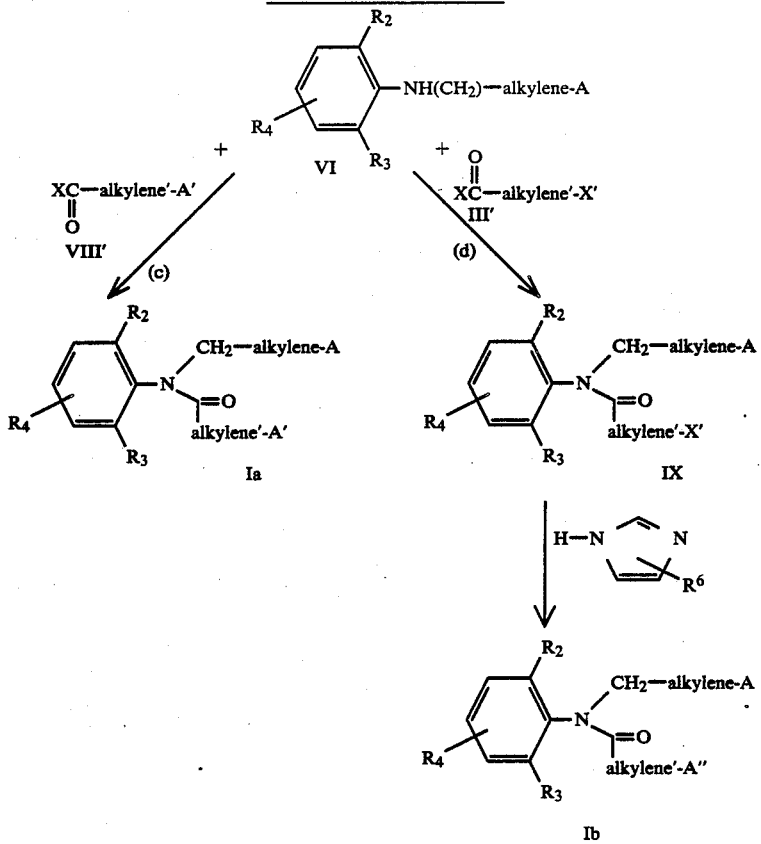

wherein $R_2$, $R_3$, $R_4$, X, X', A, A', and A" are as described above; and $R_6$ is hydrogen, lower alkyl or aryl.

In accordance with reaction pathway (c) above, a compound of formula VI, such as N-(2,6-dimethylphenyl)-1H-imidazole-1-ethanamine, can be reacted with an acid halide of formula VIII' that has been prepared in situ to obtain a compound of formula Ia. Methods of preparing acid halides of formula VIII', which are the same type acid halides but are not necessarily identical acid halides to those of formula VIII, have been described above.

A solution of an acid halide of formula VIII', for example, one prepared by reacting a solution of 3-pyridinebutanoic acid in an excess of thionyl chloride, in an organic solvent such as 1,2-dichloromethane or, more preferably dichloromethane, is treated with a compound of formula VI. After the reaction is complete the reaction mixture is diluted with base and the resulting compound of formula Ia, for example, N-(2,6-dimethylphenyl)-N-[2-(1H-imidazol -1-yl)ethyl]-3-pyridinebutanamide, can be recovered by conventional means such as crystallization.

Other compounds of formula Ia are N-(2,6-dimethylphenyl) -N-[3-(3-pyridinyl)propyl]-3-pyridinebutanamide; N-(2,6-dimethylphenyl)-N-[4-(4-pyridinyl)butyl]-3-pyridinebutanamide; and the like.

In accordance with reaction pathway(d) above, a compound of formula VI can be reacted with an acid halide of formula III' to prepare a compound of formula IX. Acid halides of formula III' are the same type acid halides but are not necessary identical to those of formula III described above. The reaction is carried out in an aprotic, organic solvent such as dimethylformamide or, more preferably, dichloromethane at about $-10°$ to about 15°. The resulting compound of formula IX can be recovered by conventional means, as by a standard work up followed by evaporation of solvent.

A compound of formula IX can be converted to a compound of formula Ib by reaction with an unsubstituted or lower alkyl or aryl substituted imidazole.

For example, a compound of formula IX can be converted to a compound of formula Ib by reaction with an alkali metal hydride and imidazole. More specifically, 2-chloro-N-(2,6-dimethylphenyl)-N-[3-(3-pyridinyl) -propyl]acetamide can be converted to N-(2,6-dimethylphenyl) -N-[3-(3-pyridinyl)propyl]-1H-imidazole-1-acetamide by reaction with sodium hydride and imidazole.

The reaction can be carried out by adding, for example, 2-chloro-N-(2,6-dimethylphenyl)-N-[3-(3-pyridinyl)propyl]-acetamide to a heated mixture of sodium hydride and imidazole in an aprotic, organic solvent, preferably dimethylformamide. The temperature of the reaction which is not critical can be about 50°. The reaction is continued until the formation of N-(2,6-dimethylphenyl)-N -[3-(3-pyridinyl)propyl]-1H-imidazole-1-acetamide is complete.

Water is added to the reaction mixture, which is then evaporated to dryness. The residue is then dissolved in an acid, such as hydrochloric acid, washed with a solvent, such as ether; made basic, and extracted with another solvent, such as dichloromethane.

The N-(2,6-dimethylphenyl)-N-[3-(3-pyridinyl)propyl]-1H-imidazole-1-acetamide can be recovered by conventional means such as crystallization.

N-(2,6-dimethylphenyl)-2-methyl-N-[3-(3-pyridinyl)-propyl]-1H-imidazole-1-acetamide may be prepared in an analogous manner by using the sodium salt of 2-methyl imidazole in place of imidazole in the process described just above.

In reaction scheme 4 there is diagrammed a process for converting a compound of formula VI into a compound of formula Ic.

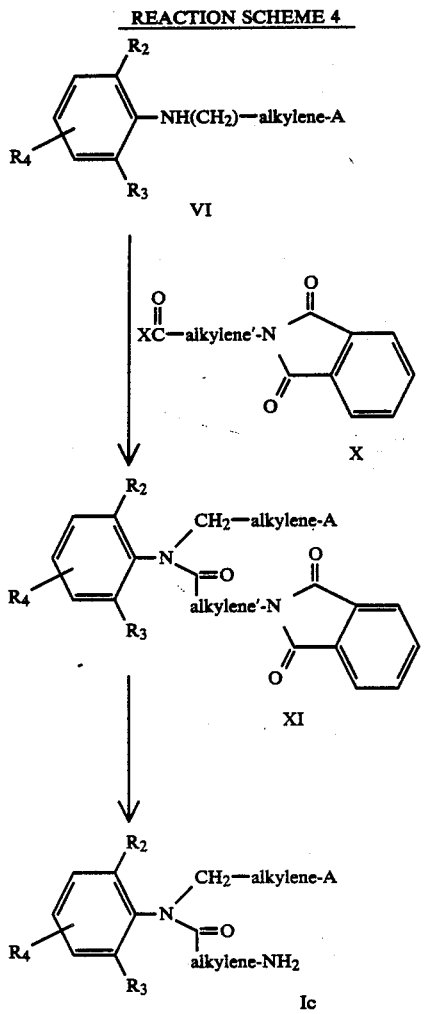

wherein $R_2$, $R_3$, $R_4$, X, and A are as described above.

In accordance with reaction Scheme 4 above, a compound of formula VI can be reacted with an acid halide of formula X to prepare a compound of formula XI. The reaction is carried out in an aprotic, organic solvent, such as chloroform, methylene chloride, or dimethylformamide. A preferred organic solvent is methylene chloride. The reaction is conducted at a temperature in the range of from about zero degrees to about room temperature, most preferably at about zero degrees. The reaction is continued until amide formation is complete. The temperature of the reaction is not critical. Recovery of a compound of formula XI can be by conventional techniques. For example, the solvent of the reaction mixture can be evaporated and the residue can be crystallized.

Exemplary of compounds of formula XI are:
rac-2,3-dihydro-N-(2,6-dimethylphenyl)-N-[4-(1H-imidazol-1-yl)-butyl]-alpha-methyl-1,3-dioxo-1H-isoindole -2-acetamide;
rac-2,3-dihydro-N-(2,6-dimethylphenyl)-alpha-methyl-1,3-dioxo -N-[4-(3-pyridinyl)butyl]-1H-isoindole-2-acetamide; and
rac-2,3-dihydro-N-(2,6-dimethylphenyl)-alpha-methyl-1,3-dioxo -N-[6-(3-pyridinyl)hexyl]-1H-isoindole-2-acetamide.

Compounds of formula X are known or can be prepared by known methods. Exemplary of compounds of formula X are 2,3-dihydro-1,3-dioxo-1H-isoindol-alpha-methylacetyl chloride; 2,3-dihydro-1,3-dioxo-1H-isoindol-alpha-methylpropionyl chloride; and the like.

A compound of formula XI can be converted to a compound of formula Ic by reaction with aqueous methylamine in a polar, aprotic organic solvent. The solvent can be, for example, dimethylsulfoxide, tetrahydrofuran, or most preferably dimethylformamide. The reaction is conducted at a temperature in the range of from about 35° to about 65°. The reaction is run for a period of time from about 1 hour to about 3 hours. Separation of a compound of formula Ic can be by conventional separatory techniques, such as crystallization.

Exemplary of compounds of formula Ic are:
rac-2-amino-N-(2,6-dimethylphenyl)-N-[4-(1H-imidazol-1-yl) butyl]propanamide;
rac-2-amino-N-(2,6-dimethylphenyl)-N-[4-(3-pyridinyl) butyl]-propanamide;
rac-2-amino-N-(2,6-dimethylphenyl)-N-[6-(3-pyridinyl) hexyl]-propanamide;
rac-2-amino-N-(2,6-dimethylphenyl)-N-[3-(3-pyridinyl) propyl]propanamide; and the like.

The compounds of Formula Ia, Ib, and Ic are encompassed by Formula I.

The compounds of formula I above form pharmaceutically acceptable acid addition salts with inorganic acids. Thus, the compounds of formula I above form pharmaceutically acceptable acid addition salts with inorganic acids, such as hydrochloric acid, hydrobromic acid, sulfuric acid and phosphoric acid. The compounds of formula I above also form pharmaceutically acceptable acid addition salts with organic acids, such as tartaric acid, oxalic acid, citric acid, camphorsulfonic acid, ethanesulfonic acid, toluenesulfonic acid, salicylic acid, ascorbic acid, maleic acid, succinic acid, formic acid, acetic acid and the like. Compounds of formula I above, including the pharmaceutically acceptable acid addition salts thereof, possess antiarrhythmic activity, and therefore are useful as antiarrhythmic agents. Compounds of formula I above, including the pharmaceutically acceptable acid addition salts thereof, also have antithrombotic activity and therefore are useful as antithrombotic agents. The compounds of formula I above, and their pharmaceutically acceptable acid addition salts also inhibit thromboxane synthase and therefore are useful in the treatment of ischemic heart disease. Some of the compounds of formula I also have blood platelet antiaggregatory properties. The pharmacologically useful activities of the compounds of the invention are demonstrated in warm-blooded animals using the procedures described below.

(1) Test for Effectiveness Against Ouabain-induced Ventricular Arrythmia

Ventricular arrhythmia in an anesthetized dog was induced by an intravenous administration of ouabain. An initial i.v. dose of 40 μg/kg was administered, then 20 μg/kg i.v. 30 minutes later and then additional 10 μg/kg i.v. every 15 minutes until ventricular arrhythmia developed. The ventricular automaticity was confirmed to be present when vagal stimulation (10 V, 30 Hz, 1 msec for 3 sec) failed to cause cardiac arrest. The test compound, which was rac.-2-amino-N-(2,6-dimethylphenyl)-N-[3-(3-pyridinyl)propyl]propanamide dihydrochloride, dissolved in saline solution, was injected into the femoral vein 10 min. after the development of the arrhythmia. The dose schedule for the test compound was 1, 3 and 10 mg/kg i.v. in this order at 15 minute intervals until the arrhythmia was reversed to sinus rhythm.

The antiarrhythmic activity of rac.-2-amino-N-(2,6-dimethylphenyl)-N-[3-(3-pyridinyl)propyl]propanamide dihydrochloride is shown in Table I.

TABLE I

Effectiveness against Ouabain-induced Ventricular Arrhythmia in Dogs

| Compound | Ouabain-induced arrhythmias No. of effective cases/No. of experiments | | | |
|---|---|---|---|---|
| | 1 | 3 | 10 | mg/kg i.v. |
| rac.-2-amino-N—(2,6-dimethylphenyl)-N—[3-(3-pyridinyl)propyl]propanamide dihydrochloride | 0/4 | 4/5 | 1/1 | 4.4 ± 1.4 was the MED mg/kg i.v. |

MED: Minimum effective dose was measured by successive injections of 1, 3 and 10 mg/kg into the femoral vein at 15 minute-intervals until ouabain-induced arrhythmia was reversed to the sinus rhythm.

(2) Test for effectiveness against ventricular arrhythmias induced by 2-stage ligation of the coronary artery in dogs (Harris dogs)

Mongrel dogs weighing between 8–14 kg were anesthetized using 30 mg/kg i.v. of sodium pentobarbital. They were artificially ventilated with room air. After thoracotomy via the fourth left intercostal space, the pericardium was opened. The left anterior descending artery was dissected free for a few millimeters near the distal edge of the particular appendage and ligated there in two stages being separated by an interval of 30 minutes. The chest was closed and the animals were allowed to recover from anesthesia for 24 hours. Ventricular premature contraction accounted for over 90% of the total number of heart beats in the conscious dogs about 24 hours after ligation. Electrograms were monitored continuously throughout the experiment and the number of ventricular and sinus beats (expressed per minute) was counted for 5 minutes every 15 or 30 minutes after p.o. administration of compound and the percentage of ventricular premature beats were calculated. During the evaluation of the antiarrhythmic effects of rac.-2-amino-N-(2,6-dimethylphenyl)-N-[3-(3-pyridinyl)propyl]propanamide dihydrochloride, the animals, which were unrestrained, were sitting on the floor quietly.

Rac.-2-amino-N-(2,6-dimethylphenyl)-N-[3-(3-pyridinyl)-propyl]propanamide dihydrochloride dramatically decreased the incidence of ventricular premature contractions (VPCs) and converted ventricular arrhythmias to sinus rhythm after oral administrations of 30 mg/kg (the number of dogs tested is 5 or n=5) and 100 mg/kg (n=5), but not at 10 mg/kg (n=4). The onset of the antiarrhythmic effects of p.o. rac.-2-amino-N-(2,6-dimethylphenyl)-N-[3-(3-pyridinyl) -propyl]propanamide dihydrochloride was approximately 1 hour (for 30 mg/kg) and 2 hours (for 100 mg/kg) and these effects lasted at least 6 hours after dosing. The maximum effects after 30 mg and 100 mg/kg were observed at 5 hours after dosing (from 94±1.5 to 13±7.9%, $p<0.01$) and at 2.5 hours (from 94±0.5 to 10±9.5%, $p<0.05$), respectively.

(3) Thromboxane A₂ synthetase inhibition, prevention of platelet aggregation and myocardial ischemia Thromboxane $A_2$ synthetase activity of a compound of the invention was demonstrated as follows. Rac.-2-amino-N-(2,6-dimethylphenyl)-N-[3-(3-pyridinyl)-propyl]propanamide dihydrochloride was tested for its inhibitory effects on thromboxane $A_2$ synthetase (washed rabbit platelet) activity in vitro.

Using washed rabbit platelets as the enzyme sources and $^{14}C$-arachidonic acid as the substrate, rac.-2-amino-N -(2,6-dimethylphenyl)-N-[3-(3-pyridinyl)propyl]-propanamide dihydrochloride was found to inhibit thromboxane $A_2$ synthetase activity with an IC50 value of 38 μM, and also inhibits the thromboxane $A_2$ synthetase activity of human platelets (using PG $H_2$ as the substrate) with an IC50 range of 1–10 μM. Therefore, rac.-2-amino-N-(2,6-dimethylphenyl)-N-[3-(3-pyridinyl)propyl]propanamide dihydrochloride is useful in the treatment of ischemic heart disease.

(4) Ex vivo experiments: Inhibition of rabbit platelet aggregation induced by collagen by the plasma of rats treated with oral rac.-2-amino-N -(2,6-dimethylphenyl)-N-[3-(3-pyridinyl)propyl]-propanamide dihydrochloride The antiplatelet aggregatory activity of rac. -2-amino-N-(2,6-dimethylphenyl)-N-[3-(3-pyridinyl) propyl]propanamide dihydrochloride was observed ex vivo in rats. Specifically, the plasma of rats which had been orally treated with rac.-2-amino-N-(2,6-dimethylphenyl) -N-[3-(3-pyridinyl)propyl]propanamide dihydrochloride for 1 hour was found to inhibit the collagen-induced rabbit platelet aggregation with an ED50 value of 123 mg/kg p.o. The results of these test are given in Table II below.

TABLE II

Ex vivo inhibition of rabbit platelet aggregation induced by collagen by the plasma of rats treated with oral rac.-2-amino-N—(2,6-dimethylphenyl)-N—[3-(3-pyridinyl)propyl]propanamide dihydrochloride

| Compound | Inhibition of collagen-induced rabbit platelet aggregation | | | |
|---|---|---|---|---|
| | Dose (mg/kg p.o.) | Number of rats | % of control[a] | ED50 in mg/kg p.o. (95% confidence limit) |
| rac.-2-amino-N—(2,6-dimethyl- | 50 | 4 | 77.1 ± 11.7 | 123 (85–274)[c] |
| | 100 | 4 | 64.8 ± 6.2[b] | |

TABLE II-continued

Ex vivo inhibition of rabbit platelet aggregation induced by collagen by the plasma of rats treated with oral rac.-2-amino-N—(2,6-dimethylphenyl)-N—[3-(3-pyridinyl)propyl]propanamide dihydrochloride

| | | Inhibition of collagen-induced rabbit platelet aggregation | | |
|---|---|---|---|---|
| Compound | Dose (mg/kg p.o.) | Number of rats | % of control[a] | ED50 in mg/kg p.o. (95% confidence limit) |
| phenyl)-N—[3-(3-pyridinyl)propyl]propanamide dihydrochloride | 200 | 4 | 40.3 ± 14.0[b] | |

[a]This column gives the % of platelet aggregation as compared to the control. The control = 100% platelet aggregation.
An aliquot (125 μl) of the platelet free plasma of the rats which had been orally treated with compound for 1 hour was added to the platelet rich plasma (125 μl) of the rabbit. Collagen (3 μg/ml) induced platelet aggregation was measured turbidimetrically.
[b]$p < 0.01$
[c]There is a 95% chance that if this experiment were run again, the ED50 found would be within the indicated range.

(5) Inhibition of Arachidonic Acid (AA) Induced Platelet Aggregation

Human platelet rich plasma (PRP) and platelet poor plasma (PPP) are prepared from 0.38% sodium citrate treated blood. PRP is obtained by centrifugation at 180×g for 10 minutes and PPP by centrifuging the remaining red cell layer 1000×g for 10 minutes. Aggregation is determined by the turbidometric method of Born G.V.R., Nature, 194, 927, (1962), and monitored at 37° C. with a Payton dual channel module with stirring speed set at 900 rpm. PRP (0.45 ml) is added to a siliconized cuvette and prewarmed to 37° C. Zero and 100% light transmission are set with PRP and PPP, respectively. AA (50 μl) is added to the stirring PRP one minute after the addition of 5 μl of the compound to be tested. A threshold dose (0.3 to 1 mM) of AA is chosen which causes maximum aggregation at about 2 minutes. The degree of aggregation is measured 2 minutes after the AA dose, which is 70-80% with AA alone. 50% inhibition of the 2 minute AA response is calculated from dose curves and represented at IC50 values. Compounds are usually run at 0.1 to 10 μM and those not active at 10 μM are designated as >10 μM. Activities of compounds of the invention in this test can be found in Table III below.

(6) Inhibition of Platelet Activating Factor (PAF) Induced Platelet Aggregation Human platelet rich plasma (PRP) and platelet poor plasma (PPP) are prepared from 0.38% sodium citrate treated blood. PRP is obtained by centrifugation at 180×g for 10 minutes and PPP by centrifuging the remaining red cell layer 1000×g for 10 minutes. Aggregation is determined by the turbidometric method of Born which was cited above, and monitored at 37° C. with a Payton dual channel module with stirring speed set at 900 rpm. PRP (0.45 ml) is added to a siliconized cuvette and prewarmed to 37° C. Zero and 100% light transmission are set with PRP and PPP, respectively. PAF (50 μl) is added to the stirring PRP one minute after the addition of 5 μl of the compound to be tested. PRP prepared from citrated human blood will aggregate when stirred in the presence of PAF giving a two phase response. The first phase is caused by PAF and the second phase is caused by the release of arachidonic acid. PAF is used at 1 μM and only the first phase response, about 30% aggregation, is evaluated. The first phase is resistant to indomethacin, 50% inhibition of the 1st phase PAF response is calculated from dose curves and represented as IC50 values. Compounds are usually run at 0.1 to 10 μM and those not active at 10 μM are designated at >10 μM. Activities of compounds of the invention in this test can be found in Table III below.

TABLE III

Antiarrhythmic Activity, Platelet Aggregation Inhibition Activity, Thromboxane Synthase Inhibition Activity of the Compounds of the Invention.

| Compound | | | Thromboxane Synthase Inh. IC50 M | Platelet Aggregation Inhibition IC50 M | | Ovabain Induced Arrhythmias MED mg/kg IV |
|---|---|---|---|---|---|---|
| R2 | R3 | R4 | | AA | PAF | |
| H | H | H | $10^{-5}$–$10^{-4}$ | — | — | >10 |
| H | H | CH3 | $10^{-5}$–$10^{-4}$ | — | — | >10 |
| CH3 | CH3 | H | $10^{-5}$–$10^{-4}$ | 5 | 20 | 4.4 ± 1.4 |

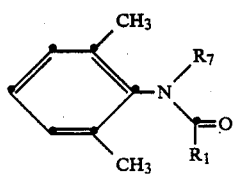

R7                R1

TABLE III-continued

Antiarrhythmic Activity, Platelet Aggregation Inhibition Activity, Thromboxane Synthase Inhibition Activity of the Compounds of the Invention.

| Compound | Thromboxane Synthase Inh. $IC_{50}$ M | Platelet Aggregation Inhibition $IC_{50}$ M AA | PAF | Ovabain Induced Arrhythmias MED mg/kg IV |
|---|---|---|---|---|
| 3-[1-aminoethyl]pyridine with −(CH$_2$)$_4$− linker (−CH(CH$_3$)NH$_2$) | $10^{-5}$–$10^{-4}$ | >10 | >10 | ½ converted at 3 mg/kg |
| 3-[1-aminoethyl]pyridine with −(CH$_2$)$_6$− linker (−CH(CH$_3$)NH$_2$) | $10^{-5}$–$10^{-4}$ | — | — | 8.3 ± 1.8 |
| −(CH$_2$)$_4$−N(imidazole), −CH(CH$_3$)NH$_2$ pyridine | ~$10^{-5}$ | >10 | >10 | >10 |
| 3-pyridyl with −(CH$_2$)$_3$−, −CH$_2$CH(CH$_3$)NH$_2$ | $10^{-6}$–$10^{-5}$ | >10 | >10 | ½ converted at 3 mg/kg |
| 3-pyridyl with −(CH$_2$)$_3$−, −CH$_2$−N(imidazole) | $10^{-7}$–$10^{-6}$ | >10 | 1 | ½ dead at 1 mg/kg |
| 3-pyridyl with −(CH$_2$)$_3$−, −CH$_2$−N(2-methylimidazole, CH$_3$) | $10^{-7}$–$10^{-6}$ | >10 | >10 | >10 |
| −(CH$_2$)$_2$−N(imidazole) / −(CH$_2$)$_3$−(3-pyridyl) | $10^{-7}$–$10^{-6}$ | 0.5 | 0.5 | ½ dead at 3 mg/kg |
| H, −CH(NH$_2$)CH$_3$ | | >100 | >100 | 15.5 ± 3.4 |

The compounds of formula I, the enantiomers thereof, the racemic mixtures thereof, or the pharmaceutically acceptable salts thereof as herein described, can be incorporated into standard pharmaceutical forms. For example, they are useful for oral or intravenous application with the usual pharmaceutical adjuvant material, for example, organic or inorganic inert carrier materials, such as water, gelatin, lactose, starch, magnesium stearate, talc, vegetable oils, gums, polyalkylene glycols, and the like. The pharmaceutical preparations can be employed in a solid form, for example, as tablets, troches, suppositories, capsules, or in liquid form, for example, as solutions, suspensions or emulsions. Pharmaceutical adjuvant materials can be added and include preservatives, stablizers, wetting or emulsifying agents, salts to change the osmotic pressure or to act as buffers. The pharmaceutical preparations can also contain other therapeutically active substances.

Representative of a method for administering the compounds of formula I is by the oral administration route. The compounds of formula I may also be administered intravenously.

A dosage range for oral administration of a compound of formula I is from about 100 mg to about 3,000 mg per day.

The compounds of formula I are qualitatively similar in their activity to tocainide, a known antiarrhythmic agent.

Those compounds of formula I which possess an asymmetric carbon atom, are ordinarily obtained as racemic mixtures. The resolution of such racemates into the optically active isomers can be carried out by known procedures. For example, diastereomers are formed from the racemic mixture with an optically active resolving agent, for example, an optically active acid, such as (+) dibenzoyltartaric acid, which can be reacted with the racemic mixture to be resolved. The formed diastereomers are separated by selective crystallization and converted to the corresponding optical isomer. Thus, the invention covers the racemic mixtures of the compounds of formula I as well as the optically active isomers, that is the enantiomers.

The following Examples further illustrate the invention. All parts are be weight and all temperatures are in degrees Celsius, unless otherwise mentioned.

Example 1

N-(2,6-Dimethylphenyl)-3-pyridinepropanamine

A solution of 194 g of 2,6-dimethylaniline and 50 g of 3-pyridinepropylbromide hydrobromide was heated to a bath temperature of 150° C. for 2 hours. The flask was fitted with a short path distillation head and the excess 2,6-dimethylaniline was removed by distillation. The residue was dissolved in 1:1 toluene/aqueous sodium hydroxide and the layers were separated. The aqueous layer was extracted with toluene and the combined organic layers were washed with 2N sodium hydroxide, and saturated sodium bicarbonate and were dried with potassium carbonate. Evaporation gave 27.0 g of N-(2,6-dimethylphenyl)-3-pyridinepropanamine as a light brown oil.

Example 2 rac.-2,3-dihydro-N-(2,6-dimethylphenyl)-alpha-methyl-1,3-dioxo-N-[3-(3-pyridinyl)propyl]-1H-isoindole-2-acetamide hydrochloride A solution of 10 g of N-(2,6-dimethylphenyl)-3-pyridine propanamine in dichloromethane was cooled in an ice bath and was treated with 10.4 g of 2,3-dihydro-1,3-dioxo-1H -isoindole-alpha-methylacetyl chloride. The reaction mixture was stirred at 0° C. for 10 minutes and allowed to warm to room temperature overnight. The solvent was evaporated and the residue was crystallized from methanol-ether to give 15.6 g of rac.-2,3-dihydro-N -(2,6-dimethylphenyl)-alpha-methyl-1,3-dioxo-N-[3-(3-pyridinyl) propyl]-1H-isoindole-2-acetamide-hydrochloride, mp 220°-223° C. Recrystallization from methanol-ether afforded 13.55 g of captioned product, mp 223°-225° C.

Example 3 rac.-2-amino-N-(2,6-dimethylphenyl)-N-[3-(3-pyridinyl) -propyl]propanamide dihydrochloride To a solution of 45.0 g of rac-2,3-dihydro-N-(2,6-dimethylphenyl)-alpha-methyl-1,3-dioxo-N-[3-(3-pyridinyl) -propyl]-1H-isoindole-2-acetamide hydrochloride dissolved in 200 ml of dimethylformamide was added 100 ml of 40% aqueous methylamine. The reaction mixture was stirred overnight, diluted with water, and extracted twice with dichloromethane. The combined organic layers were washed with water, dried with potassium carbonate, and evaporated to give an oil. The oil was converted to the dihydrochloride salt and crystallized from methanol ether to give 23.25 g of rac.-2-amino-N-(2,6-dimethylphenyl)-N-[3-(3-pyridinyl) -propyl]propanamide dihydrochloride, mp 256°-260° C. The mother liquors afforded an additional 4.9 g, mp 256°-259° C.

Example 4

N-(2,6-Dimethylphenyl)-3-pyridinehexanamide

To an ice cooled solution of 33.5 ml of thionyl chloride was added 30.0 g of 3-pyridinehexanoic acid in portions. The resulting pale green solution was heated to reflux for 10 minutes and was concentrated under reduced pressure. Two portions of toluene were added and evaporated to remove the last of the thionyl chloride giving an orange solid which was dissolved in 750 ml of dry dichloromethane and added over a 30 minute period to a solution of 20 ml of 2,6-dimethylaniline in 200 ml of dry dichloromethane and 25 ml of dry triethylamine. The reaction mixture was stirred overnight at room temperature, diluted with 750 ml of water and made basic with 5N sodium hydroxide solution. The layers were separated, the aqueous layer extracted with dichloromethane and the combined organic layers were washed with water, dried with potassium carbonate and evaporated to a solid which was recrystallized from ethyl acetate-hexane to give 38.3 g of N-(2,6-dimethylphenyl)-3-pyridinehexanamide, mp 98°-100° C.

Example 5

N-(2,6-Dimethylphenyl)-3-pyridinebutanamide

To an ice cooled solution of an excess of thionyl chloride was added 15.0 g of pyridinebutanoic acid in portions. The resulting solution was heated to reflux for 10 minutes and was concentrated under reduced pressure. Two portions of toluene were added and evaporated to remove the last of the thionyl chloride giving a solid which was dissolved in dry dichloromethane and added over a 30 minute period to a solution of 11.0 g of 2,6-dimethylaniline in dry dichloromethane and dry triethylamine. The reaction mixture was stirred overnight at room temperature, diluted with water and made basic with 5N sodium hydroxide solution. The layers were separated, the aqueous layer extracted with dichloromethane and the combined organic layers were washed with water, dried with potassium carbonate and evaporated to give a black oil which was chromatographed on silica gel eluting with ethyl acetate. The product was recrystallized from dichloromethane-ether to give 19.6 g of the free base N-(2,6-dimethylphenyl) -3-pyridinebutanamide, mp 98°-99° C. The hydrobromide salt was crystallized from 2-propanol, mp 188°-190° C. cl Example 6

N-(2,6-Dimethylphenyl)-3-pyridinebutanamine(E)-2-butenedioate (1:2) salt

A solution of 13.9 g of N-(2,6-dimethylphenyl)-3-pyridinebutanamide in dry tetrahydrofuran was added dropwise with stirring to an excess of 1 molar borane in tetrahydrofuran and the resulting solution was heated to reflux for two hours. After cooling, excess methanol was added to decompose the remaining borane and the solution was evaporated to dryness. The residue was acidified by the cautious addition of 2N hydrochloric acid and was warmed on the steam bath for 20 minutes. The resulting solution was cooled, made strongly basic with sodium hydroxide solution and was extracted with dichloromethane. The combined layers were dried with potassium carbonate and concentrated to give N-(2,6-dimethylphenyl)-3-pyridine-butanamine as an oil. A solution of the free base in methanol was treated with an excess of fumaric acid in methanol and the resulting solution was diluted with ether. The resulting difumarate was crystallized from 200 ml of 2-propanol to give 20.6 g of N-(2,6-dimethylphenyl) -3-pyridinebutanamine (E)-2-butenedioate(1:2) salt, mp 138°–140° C. (decomposition). Recrystallization from 2-propanol gave the analytical sample, mp 140°–142° C. (decomposition).

Example 7

N-(2,6-Dimethylphenyl)-3-pyridinehexanamine

N-(2,6-Dimethylphenyl)-3-pyridinehexanamine was prepared in a manner similar to that employed above for preparing N-(2,6-dimethylphenyl)-3-pyridinebutanamine. Starting with 6.4 g of N-(2,6-dimethylphenyl)-3-pyridinehexanamide, there was obtained 3.6 g of a yellow oil which was purified by silica gel chromatography eluting with 1:1 ethyl acetate-hexane to give 2.8 g of N-(2,6-dimethylphenyl) -3-pyridinehexanamine as an oil, bp 215°–230° C./0.1 mm.

Example 8 rac.-2,3-Dihydro-N-(2,6-dimethylphenyl)-alpha-methyl-1,3-dioxo-N-[4-(3-pyridinyl)butyl]-1H-isoindole-2-acetamide hydrochloride hemihydrate N-(2,6-dimethylphenyl)-3-pyridinebutanamine was prepared by partitioning 13.0 grams of the difumarate salt between 1N sodium hydroxide and dichloromethane, drying the organic phase with potassium carbonate and concentration.

The acid chloride prepared from 8.5 g of 2,3-dihydro -1,3-dioxo-1H-isoindole-alpha-methyl-2-acetic acid by the action of excess thionyl chloride at reflux for 30 minutes followed by concentration and evaporation with two portions of toluene, was dissolved in dichloromethane, A solution of N-(2,6-dimethylphenyl)-3-pyridinebutanamine in dichloromethane was added and the resulting solution was stirred 2 hours and diluted with excess 1N sodium hydroxide. The organic phase was washed with water, dried with sodium sulfate and concentrated. There was obtained 13.6 g of an oil. Conversion to the hydrochloride salt and crystallization from ethanol-ether gave 12.1 g of rac.-2,3-dihydro-N-(2,6-dimethylphenyl)-alpha-methyl-1,3-dioxo-N-[4-(3-pyridinyl)butyl]-1H-isoindole-2-acetamide hydrochloride hemihydrate mp 203°–206° C. Recrystallization from 2-propanol-ether gave the analytical sample, mp 209°–211° C.

Example 9 rac.-2,3-Dihydro-N-(2,6-dimethylphenyl)-alpha-methyl-1,3-dioxo-N-[6-(3-pyridinyl)hexyl]-1H-isoindole-2-acetamide A solution of 1.7 g of 2,3-dihydro-1,3-dioxo-1H -isoindole-alpha-methyl-acetyl chloride in 20 ml of dry dichloromethane was added dropwise to a solution of 2.0 g N-(2,6-dimethylphenyl)-3-pyridinehexanamine in 20 ml of dichloromethane. The reaction mixture was stirred overnight at room temperature, diluted with water and aqueous sodium hydroxide and the layers were separated. The aqueous layer was extracted with dichloromethane and the combined organic layers were washed with water, dried with potassium carbonate and concentrated. The residue was crystallized from ethyl acetate-hexane to give 2.3 g of rac.-2,3-dihydro-N-(2,6-dimethylphenyl)-alpha-methyl-1,3-dioxo-N-[6-(3-pyridinyl)hexyl]-1H-isoindole-2-acetamide, mp 113°–115° C.

Example 10 rac.-2-amino-N-(2,6-dimethylphenyl)-N-[4-(3-pyridinyl)butyl]-propanamide dihydrochloride The free base of the captioned compound was prepared by dissolving rac.-2,3-dihydro-N-(2,6-dimethylphenyl)-alpha -methyl-1,3-dioxo-N-[4-(3-pyridinyl)-butyl]-1H-isoindole-2-acetamide (E)-2-butenedioate (2:1) salt hemihydrate in methylene chloride, adding 1N sodium hydroxide, drying the organic layer with potassium carbonate, and evaporation to give an oil. Dimethylformamide was added, followed by an excess of 30% aqueous methylamine, and the solution was heated at 50° C. for 2 hours. The dimethylformamide was evaporated and the residue was dissolved in 0.5N hydrochloric acid and was washed several times with dichloromethane. The organic layers were extracted in turn with 0.5N hydrochloric acid and then discarded. The combined aqueous layers were made basic with excess sodium hydroxide and the product was extracted with dichloromethane. The organic layers were washed with brine, dried with potassium carbonate and evaporated to give a free base as an oil.

The free base in 2-propanol was treated with 2.1 molar equivalents of ethanolic hydrochloric acid and the dihydrochloride salt slowly crystallized. 7.1 g of rac.-2-amino-N-(2,6-dimethylphenyl)-N-[4-(3-pyridinyl)butyl] -propanamide dihydrochloride was obtained, mp 236°–237° C. (decomposition).

Example 11 rac.-2-Amino-N-(2,6-dimethylphenyl)-N-[6-(3-pyridinyl)hexyl]-propanamide 0.4 methanolate rac.-2-Amino-N-(2,6-dimethylphenyl)-N-[6-(3-pyridinyl) -hexyl]propanamide 0.4 methanolate was prepared in a manner similar to that employed for the preparation of rac.-2-amino-N-(2,6-dimethylphenyl)-N-[4-(3-pyridinyl)butyl]-propanamide above. From 10.75 g of rac.-2,3-dihydro-N -(2,6-dimethylphenyl)-alpha-methyl-1,3-dioxo-N-[6-(3-pyridinyl)hexyl]-1H-isoindole-2-acetamide there was obtained 8.6 g of an oil which was purified by preparative high pressure liquid chromatography using silica gel columns and eluting with 95:5:1 dichloromethane -methanol-triethylamine. The product was a yellow oil which was dried under vacuum to give 6.45 g of rac.-2-amino-N-(2,6-dimethylphenyl)-N-[6-(3-pyridinyl)hexyl]propanamide 0.4 methanolate.

Example 12

N-(2,6-Dimethylphenyl)-1H-imidazole-1-butanamide hydrobromide salt

Trifluoroacetic acid (35 ml) was stirred while adding 8.8 g of solid 1H-imidazole-1-butanoic acid followed by 25 ml of trifluoroacetic anhydride. The solution was stirred for 15 minutes and evaporated in vacuo at room temperature. The residual acid was removed by re-evaporation with toluene and the resulting mixed anhydride was dissolved in 50ml of dimethylformamide. A solution 15.2 g of 2,6-dimethylaniline in 15 ml of dimethylformamide was added and the mixture was stirred for 15 minutes. The solution was evaporated to dryness and the residue was partitioned between dichloromethane and saturated sodium bicarbonate. The organic layer was dried with potassium carbonate and evaporated to an oil which was dissolved in 50 ml of 2-propanol and acidified with 1.1 molar equivalents of 2N hydrobromic acid in 2-propanol solution. Dilution with ether provided 13.1 g of N-(2,6-dimethylphenyl)-1H-imidazole -1-butanamide hydrobromide salt, mp 172°-174° C. Recrystallization from 2-propanol/ether provided the analytically pure salt, mp 176°-177° C.

Example 13

N-(2,6-Dimethylphenyl)-1H-imidazole-1-butanamine(E)-2-butenedioate (1:2) salt

A solution of 27.27 g of N-(2,6-dimethylphenyl)-1H -imidazole-butanamide hydrobromide salt in 250 ml of dry tetrahydrofuran was added dropwise with stirring to 530 ml of 1 molar borane in tetrahydrofuran and the resulting solution was heated to reflux for 2 hours. After cooling, excess methanol was added to decompose the remaining borane and the solution was evaporated to dryness. The residue was acidified by the cautions addition of 285 ml of 2N hydrochloric acid and was warmed on the steam bath for 20 minutes. The resulting solution was cooled, made strongly basic with sodium hydroxide solution and was extracted with dichloromethane. The combined organic layers were dried with potassium carbonate and concentrated to give 25.1 g of N-(2,6-dimethylphenyl)-1H-imidazole-1-butanamine as an oil which was dissolved in 200 ml of methanol, treated with 23.9 g of fumaric acid and diluted with 600 ml of ether. The resulting solid amounted to 37.0 g of N-(2,6-dimethylphenyl) -1H-imidazole-1-butanamide (E)-2-butenedioate(1:2) salt, mp 146°-147° C. Recrystallization from methanol-ether gave the analytical sample, mp 148°-149° C.

Example 14 rac.-2,3-Dihydro-N-(2,6-dimethylphenyl)-N-[4-(1H-imidazol -1-yl)butyl]-alpha methyl-1,3-dioxo-1H-isoindole-2-acetamide (E)-2-butenedioate (2:1) salt hemihydrate The free base of N-(2,6-dimethylphenyl)-1H-imidazole -1-butanamine was prepared by partitioning 22.4 g of its difumarate salt between 1N sodium hydroxide and dichloromethane, drying the organic phase with potassium carbonate and concentration.

The acid chloride prepared from 12.0 g of 2,3-dihydro -1,3-dioxo-1H-isoindole-alpha-methyl-2-acetic acid by the action of excess thionyl chloride at reflux for 30 minutes followed by concentration and evaporation with two portions of toluene was dissolved in 50 ml of dichloromethane. A solution of the above N-(2,6-dimethylphenyl)-1H-imidazole -1-butanamine in 50 ml of dichloromethane was added and the resulting solution was stirred 2 hours and diluted with excess 1N sodium hydroxide. The organic phase was washed with water, dried with sodium sulfate and concentrated to give 18.7 g of a yellow oil. The free base was treated with 2.38 g of fumaric acid in 100 ml of ethanol. Dilution with 200 ml of ether afforded 16.1 g of rac.-2,3-dihydro-N-(2,6-dimethylphenyl)-N-[4-(1H-imidazol-1-yl)butyl]-alpha-methyl -1,3-dioxo-1H-isoindole-2-acetamide (E)-2-butenedioate (2:1) salt hemihydrate, mp 151°-153° C.

Example 15 rac.-2-Amino-N-(2,6-dimethylphenyl)-N-[4-(1H-imidazol-1-yl) -butyl]propanamide dihydrochloride Rac.-2-amino-N-(2,6-dimethylphenyl)-N-[4-(1H-imidazol-1-yl)butyl]propanamide was prepared from 16.1 g of hemifumarate by partitioning the salt between methylene chloride and 1N sodium hydroxide, drying the organic layer with potassium carbonate, and evaporation to give 13.8 g of oil. Dimethylformamide (100 ml) was added, followed by 30 ml of 30% aqueous methylamine, and the solution was heated at 50° C. for 2 hours. The dimethylformamide was evaporated and the residue was dissolved in 100 ml of 0.5N hydrochloric acid and was washed several times with dichloromethane. The organic layers were extracted in turn with 0.5N hydrochloric acid and then discarded. The combined aqueous layers were made basic with excess sodium hydroxide and the product was extracted with dichloromethane. The organic layers were washed with brine, dried with potassium carbonate and evaporated to give 9.2 g of free base as an oil.

The free base in 100 ml of 2-propanol was treated with 2.1 molar equivalents of ethanolic hydrochloride acid and the dihydrochloride salt slowly crystallized. Filtration of the chilled mixture gave 10.8 g of rac.-2-amino-N-(2,6-dimethylphenyl-N-[4-(1H-imidazol-1-yl)butyl]propanamide dihydrochloride, mp 225°-226° C. Recrystallization from 2-propanol provided the analytically pure dihydrochloride salt, mp 225°-226° C.

Example 16

N-(2,6-Dimethylphenyl)-1H-imidazole-1-acetamide

A mixture of 6.0 g of a 60% oil dispersion of sodium hydride in 90 ml of dimethylformamide was stirred and heated at 50° C. during the portionwise addition of 10.32 g of imidazole. After stirring for 20 minutes, 15.0 g of 2-chloro-N-(2,6-dimethylphenyl)acetamide was added and heating was continued for an additional 30 minutes. Water was added and the reaction mixture was evaporated to dryness. The residue was dissolved in 2N hydrochloric acid, washed with ether, made strongly basic with excess sodium hydroxide and the product was extracted with dichloromethane. The combined organic layers were dried with sodium sulfate and evaporated to give 14 g of N-(2,6-dimethylphenyl)-1H-imidazole-1-acetamide, mp 160°-162° C.

The free base (4.0 g) in 50 ml of 2-propanol was treated with excess 4N ethanolic-hydrochloric acid solution and 50 ml of ether was added. The resulting solid was recovered by filtration and recrystallized from 1:1 2-propanol-ether to give 3.8 g of the analytically pure hydrochloride salt of N-(2,6-dimethylphenyl)-1H-imidazole-1-acetamide, mp 198°-200° C.

Example 17

N-(2,6-Dimethylphenyl)-1H-imidazole-1-ethanamine

A mixture of 9.2 g of N-(2,6-dimethylphenyl)-1H -imidazole-1-acetamide in 200 ml of 1 molar borane.tetrahydrofuran complex was refluxed for 2 hours and chilled in ice. Excess methanol was added to decompose the remaining borane and the solution was evaporated to dryness. The residue was cautiously treated with 125 ml of 2N aqueous hydrochloric acid and was warmed gently on the steam bath for 20 minutes. After cooling and treatment with excess 4N sodium hydroxide the product was extracted with dichloromethane, dried with potassium carbonate, and evaporated. Crystallization of a small portion from ether-hexane provided the analytically pure free base, mp 57°–59° C.

The bulk of free base was dissolved in 100 ml of 2-propanol, treated with 2.2 molar equivalents of 4N ethanolic-hydrochloric acid and diluted with an equal volume of ether to give 10 g of dihydrochloride salt of N-(2,6-Dimethylphenyl)-1H-imidazole-1-ethanamine, mp 207°–210° C.

Example 18

N-(2,6-Dimethylphenyl)-N-[2-(1H-imidazol-1-yl)ethyl]-3-pyridinebutanamide

A solution of 7.0 g of 3 pyridinebutanoic acid in excess thionyl chloride was heated to reflux for 30 minutes and was concentrated, diluted with toluene and evaporated to dryness. The residue was dissolved in 30 ml of dichloromethane and treated with a solution of N-(2,6-dimethylphenyl)-1H-imidazole-1-ethanamine in 50 ml of dichloromethane which was prepared by partitioning 9.8 g of the dihydrochloride salt of N-(2,6-dimethylphenyl)-1H -imidazole-1-ethanamine between 1N sodium hydroxide and dichloromethane. After 2 hours, the reaction mixture was diluted with 1N sodium hydroxide and the organic phase was washed with water, dried with sodium sulfate and concentrated. The residue was taken up in ethyl acetate, charcoaled, and diluted with hexane to give 9.5 g of N-(2,6-dimethylphenyl)-N-[2-(1H-imidazol-1-yl)ethyl]-3-pyridinebutanamide mp 104°–106° C. The analytical sample was obtained from ethyl acetate-hexane, mp 108°–110° C.

Example 19

2-Chloro-N-(2,6-dimethylphenyl)-N-[3-(3-pyridinyl)-propyl]-acetamide

A solution of 10.0 g of N-(2,6-dimethylphenyl)-3-pyridinepropanamine in 75 ml of dichloromethane was added dropwise to a cold (0° C.) solution of 3.5 ml of chloroacetylchloride in 35 ml of dichloromethane. The cooling bath was removed and the reaction was allowed to warm to room temperature over 30 minutes followed by the addition of excess aqueous sodium bicarbonate solution. The layers were separated and the organic layer was washed with brine, dried with sodium sulfate and evaporated to give 13.4 g of product as a dark oil which was used directly in the next steps, that is, in Examples 20 and 21.

Example 20

N-(2,6-Dimethylphenyl)-N-[3-(3-pyridinyl)propyl]-1H-imidazole-1-acetamide dihydrochloride A mixture of 1.68 g of 60% sodium hydride in oil dispersion and 2.86 g of imidazole in 25 ml of dimethylformamide was heated at 50° C. for 15 minutes to give a clear solution. A solution of 6.7 g of 2-chloro-N -(2,6-dimethylphenyl-N-[3-(3-pyridinyl)propyl]acetamide in 25 ml of dimethylformamide was added dropwise to the hot solution and heating was continued for 30 minutes. Water (25 ml) was added and the solvents were removed in vacuo. The residue, in water, was extracted with dichloromethane, washed with water, and evaporated. The product was dissolved in 50 ml of 2N hydrochloric acid and washed with ether. The aqueous solution was made basic with excess sodium hydroxide, extracted with dichloromethane, dried with sodium sulfate and evaporated to give 6.5 g of dark red oil. Partial purification was effected by filtration through 65 g of silica gel eluting with triethylamine/ methanol/ethyl acetate, (2:5:100). After evaporation, the residue (5.8 g) in 2-propanol (50 ml) was treated with 2.1 molar equivalents of ethanolic hydrochloric acid and diluted with an equal volume of ether to give 5.0 g of the dihydrochloride salt of N-(2,6-dimethylphenyl)-N-[3-(3-pyridinyl)propyl]-1H-imidazole-1-acetamide. Recrystallization from 2-propanol provided 4.7 g of the analytically pure salt, mp 241°–242° C.

Example 21

N-(2,6-Dimethylphenyl)-2-methyl-N-[3-(3-pyridinyl)-propyl]-1H -imidazole-1-acetamide This material was prepared in an analogous manner as the previous example from 2.9 g of 2-chloro-N-(2,6-dimethylphenyl)-N-[3-(3-pyridinyl)propyl]acetamide and the sodium salt of 2-methyl imidazole. After filtration through silica gel, the residue (3 g) was crystallized from ethyl acetate-hexane to give 2.1 g of analytically pure free base, mp 89°–90° C.

Example 22 rac.-2,3-Dihydro-N-(2,6-dimethylphenyl)-beta-methyl-1,3-dioxo -N-[3-(3-pyridinyl)propyl]-1H-isoindole-2-propanamide 0.7 hydrochloride hemihydrate Starting with 5.6 g of 2,3-dihydro-1,3-1H-isoindole-beta -methyl-3-propionic acid and 5.0 g of N-(2,6-dimethylphenyl-3-pyridinepropanamine, the method described for the preparation of rac.-2,3-dihydro-N-(2,6-dimethylphenyl) -N-[4-(1H-imidazol-1-yl)butyl]-alpha-methyl-1,3-dioxo-1H-isoindole-2-acetamide was employed. The product was converted to the hydrochloride salt and crystallized from ethanol-ether to give 9.4 g of rac.-2,3-dihydro-N-(2,6-dimethylphenyl) -beta-methyl-1,3-dioxo-N -[3-(3-pyridinyl)propyl]-1H-isoindole-2-propanamide 0.7 hydrochloride hemihydrate, mp 169°–171° C.

Example 23 rac.-3-Amino-N-(2,6-dimethylphenyl)-N-[3-(3-pyridinyl)propyl]-butanamide (E)-2-butenedioate (2:1) salt Starting with 9.0 g of rac.-2,3-dihydro-N-(2,6-dimethylphenyl)-beta-methyl-1,3-dioxo-N-[3-(3-pyridinyl) -propyl]-1H-isoindole-2-propanamide 0.7 hydrochloride hemihydrate and employing the method described for the preparation of rac.-2-amino-N-(2,6-dimethylphenyl)-N -[4-(1H-imidazol-1-yl)butyl]propanamide dihydrochloride, there was obtained 4.7 g of an oil which was treated with 0.83 g of fumaric acid to form the hemifumarate of rac.-3-amino-N-(2,6-dimethylphenyl)-N-[3-(3-pyridinyl) -propyl]-butanamide which was crystallized from 2-propanol -ether to give 4.8 g, mp 168°–169° C.

Example 24

| TABLET FORMULATION (Wet Granulation) | | | |
|---|---|---|---|
| Item | Ingredients | mg/tablet | mg/tablet | mg/tablet |
| 1. | rac.-2-amino-N— (2,6-dimethylphenyl)- N—[3-(3-pyridinyl) | | | |

TABLET FORMULATION (Wet Granulation)

| Item | Ingredients | mg/tablet | mg/tablet | mg/tablet |
|---|---|---|---|---|
| | propyl]propanamide dihydrochloride | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Weight of tablet | 245 mg | 490 mg | 795 mg |

Procedure:
(1) Mix items 1, 2, 4 and 5 in a suitable mixer, granulate with polyvinyl pyrrolidone and dissolve in water/alcohol. Dry the granulation. Mill the dry granulation through a suitable mill.
(2) Add magnesium stearate and compress on a suitable press.

Example 25

TABLET FORMULATION: (Direct Compression)

| Item | Ingredients | mg/tablet | mg/tablet | mg/tablet |
|---|---|---|---|---|
| 1. | rac.-2-amino-N—(2,6-dimethylphenyl)-N—[3-(3-pyridinyl)propyl]propanamide dihydrochloride | 15 | 30 | 60 |
| 2. | Lactose | 207 | 192 | 162 |
| 3. | Avicel | 45 | 45 | 45 |
| 4. | Direct Compression Starch | 30 | 30 | 30 |
| 5. | Magnesium stearate | 3 | 3 | 3 |
| | Weight of tablet | 300 mg | 300 mg | 300 mg |

Procedure:
(1) Mix Item 1 with equal amount of lactose. Mix well.
(2) Mix with Items 3, 4, and remaining amount of Item 2. Mix well.
(3) Add magnesium stearate and mix for 3 minutes.
(4) Compress on a suitable punch.

Example 26

CAPSULE FORMULATION

| Item | Ingredients | mg/capsule | mg/capsule | mg/capsule |
|---|---|---|---|---|
| 1. | rac.-2-amino-N—(2,6-dimethylphenyl)-N—[3-(3-pyridinyl)propyl]propanamide dihydrochloride | 15 | 30 | 60 |
| 2. | Lactose | 239 | 224 | 194 |
| 3. | Starch | 30 | 30 | 30 |
| 4. | Talc | 15 | 15 | 15 |
| 5. | Magnesium stearate | 1 | 1 | 1 |
| | Capsule fill weight | 300 mg | 300 mg | 300 mg |

Procedure:
(1) Mix items 1-3 in a suitable mixer.
(2) Add talc and magnesium stearate and mix for a short period of time.
(3) Encapsulate on an appropriate encapsulation machine.

Example 27

TABLET FORMULATION (Wet granulation)

| Item | Ingredients | mg/tablet | mg/tablet | mg/tablet |
|---|---|---|---|---|
| 1. | rac.-2-amino-N—(2,6-dimethylphenyl)-N—[4-(3-pyridinyl)butyl]propanamide dihydrochloride | 100 | 250 | 500 |
| 2. | Lactose | 98.5 | 147.5 | 170 |
| 3. | Polyvinyl pyrrolidone | 15 | 30 | 40 |
| 4. | Modified starch | 15 | 30 | 40 |
| 5. | Corn starch | 15 | 30 | 40 |
| 6. | Magnesium stearate | 1.5 | 2.5 | 5 |
| | Capsule fill weight | 245 mg | 490 mg | 795 mg |

Procedure:
(1) Mix items 1, 2, 4 and 5 in a suitable mixer, granulate with polyvinyl pyrrolidone and dissolve in water/alcohol. Dry the granulation. Mill the dry granulation through a suitable mill.
(2) Add magnesium stearate and compress on a suitable press.

Example 28

TABLET FORMULATION (Direct Compression)

| Item | Ingredients | mg/tablet | mg/tablet | mg/tablet |
|---|---|---|---|---|
| 1. | rac.-2-amino-N—(2,6-dimethylphenyl)-N—[4-(3-pyridinyl)butyl]propanamide dihydrochloride | 150 | 250 | 500 |
| 2. | Lactose | 207 | 192 | 162 |
| 3. | Avicel | 45 | 45 | 45 |
| 4. | Direct Compression Starch | 30 | 30 | 30 |
| 5. | Magnesium stearate | 3 | 3 | 3 |
| | Weight of tablet | 435 mg | 520 mg | 740 mg |

Procedure:
(1) Mix Item 1 with equal amount of lactose. Mix well.
(2) Mix with Items 3, 4, and remaining amount of Items 2. Mix well.
(3) Add magnesium stearate and mix for 3 minutes.
(4) Compress on a suitable punch.

Example 29

CAPSULE FORMULATION

| Item | Ingredients | mg/capsule | mg/capsule | mg/capsule |
|---|---|---|---|---|
| 1 | rac.-2-amino-N—(2,6-dimethylphenyl)-N—[4-(3-pyridinyl)butyl]propanamide dihydrochloride | 15 | 30 | 60 |
| 2. | Lactose | 239 | 224 | 194 |
| 3. | Starch | 30 | 30 | 30 |
| 4. | Talc | 15 | 15 | 15 |
| 5. | Magnesium stearate | 1 | 1 | 1 |
| | Capsule fill weight | 300 mg | 300 mg | 300 mg |

Procedure:
(1) Mix items 1-3 in a suitable mixer.
(2) Add talc and magnesium stearate and mix for a short period of time.

(3) Encapsulate on an appropriate encapsulation machine.

We claim:

1. A compound of the formula

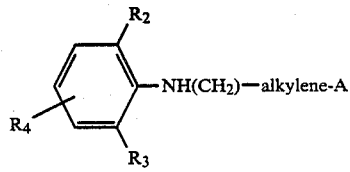

VI wherein alkylene is a straight chain alkylene of 1–5 carbon atoms optionally substituted with one or more lower alkyl substituents, $R_2$, $R_3$ and $R_4$ are, independently, hydrogen or methyl;

A is 3-pyridinyl which is unsubstituted or substituted by lower alkyl, phenyl or naphthyl.

2. A compound in accordance with claim 1, N-(2,6-dimethylphenyl)-3-pyridinepropanamine.

* * * * *